(12) United States Patent
Chiang et al.

(10) Patent No.: US 7,332,092 B2
(45) Date of Patent: Feb. 19, 2008

(54) METHOD OF SEPARATING E AND Z ISOMERS OF AN ALKENE ALCOHOL AND DERIVATIVES THEREOF

(75) Inventors: Chen-Chou Chiang, Wexford, PA (US); Elad Shabtai, DN Shikmim (IL)

(73) Assignees: Calgon Carbon Corporation, Pittsburgh, PA (US); InnovaAroma SA, Geneva (CH)

( * ) Notice: Subject to any disclaimer, the term of this patent is extended or adjusted under 35 U.S.C. 154(b) by 0 days.

(21) Appl. No.: 11/683,050

(22) Filed: Mar. 7, 2007

(65) Prior Publication Data

US 2007/0155993 A1 Jul. 5, 2007

Related U.S. Application Data

(62) Division of application No. 11/115,359, filed on Apr. 27, 2005, now Pat. No. 7,211,703.

(51) Int. Cl.
*B01D 15/04* (2006.01)
*C07C 29/74* (2006.01)
*C07C 29/76* (2006.01)
*C07C 27/26* (2006.01)

(52) U.S. Cl. .................. 210/690; 568/913; 568/917; 568/918; 568/693; 568/410; 568/408; 568/492; 560/218; 560/248; 210/660; 210/661; 210/663

(58) Field of Classification Search .............. 568/913, 568/917, 918, 693, 410, 408, 492; 560/218, 560/248; 210/660, 661, 663, 690
See application file for complete search history.

(56) References Cited

U.S. PATENT DOCUMENTS 3,600,453 A 8/1971 Reichenbacher
4,433,195 A 2/1984 Kulprathipanja
4,443,231 A 4/1984 Siegell
5,676,826 A 10/1997 Rossiter et al.

OTHER PUBLICATIONS

R. Adlof, et al., "Fractionation of Cis- and Trans-Oleic, Linoleic, and Conjugated Linoleic Fatty Acid Methyl Esters by Silver Ion High-Performance Liquid Chromatography", Journal of Chromatography, vol. 799, No. 1-2, XP-004111398, Mar. 13, 1998, pp. 329-332.

B. Nikolova-Damyanova, et al., "Silver Ion High-Performance Liquid Chromatography of Esters and Isomeric Octadecenoic Fatty Acids With Short-Chain Monounsaturated Alcohols", Journal of Chromatography, vol. 693, No. 2, XP-004023453, Feb. 24, 1995, pp. 235-239.

"Separation of Saturated, Unsaturated, and Acetylenic Fatty Acid Isomers by Silver Resin Chromatography", Journal of the American Oil Chemists' Society, 1978, 55(7), pp. 561-563.

Adlof, R. O., et al., J. Amer. Oil Chemists' Soc., vol. 57 (9), 1980, pp. 273-275.

Emken, E.A., et al., J. Amer. Oil Chemists' Soc., vol. 41 (5), 1964, pp. 388-390.

Warthen, J. David, Jr., of Chromatographic Science, vol. 14 (11), 1976, pp. 513-515.

*Primary Examiner*—Elvis O. Price
(74) *Attorney, Agent, or Firm*—Oblon, Spivak, McClelland, Maier & Neustadt, P.C.

(57) ABSTRACT

E and Z isomers of alkene alcohols and/or alkene alcohol derivatives are separated by substantially continuously contacting an ion exchange medium which is ion exchanged with silver and/or copper ions with the feed stream comprising the E and Z isomers of at least one alkene alcohol and/or at least one alkene alcohol derivative, then removing a product stream having a higher concentration of the E or Z isomer of at least one alkene alcohol or derivative of the alkene alcohol relative to the concentration of the E or Z isomer of the alkene alcohol or derivative of the alkene alcohol in the feed stream.

19 Claims, 1 Drawing Sheet

FIGURE
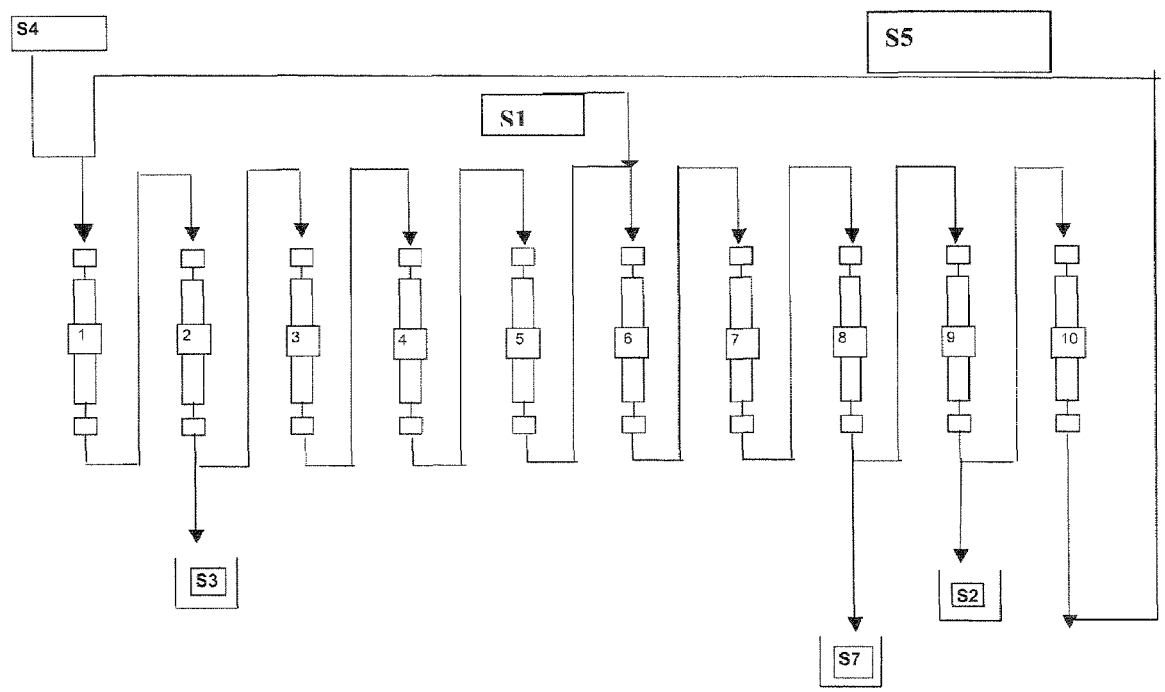

METHOD OF SEPARATING E AND Z ISOMERS OF AN ALKENE ALCOHOL AND DERIVATIVES THEREOF

BACKGROUND OF THE INVENTION

1. Field of the Invention

The present invention is a substantially continuous process for separating E and Z isomers of an alkene alcohol and derivatives thereof. An ion exchange medium which has been ion exchanged with silver and/or copper ions is contacted with a feed stream comprising a mixture of E and Z isomers of the alkene alcohol or derivative thereof as well as other components in a non-batch or substantially continuous mode, thereby enriching the resulting product stream in either the E or Z isomer.

2. Discussion of the Background

Synthetic methods for preparing unsaturated compounds which can exist in E and Z isomeric form usually provide a mixture of both isomers, yet quite often only one of these isomers is commercially valuable. It is therefore desirable to separate mixtures of E and Z isomers at commercially useful scales, and in a manner which is compatible with other processes.

Different methods have been used to separate mixtures of E and Z isomers. For example, E and Z isomers have been separated by fractional crystallization, precipitation, fractional distillation, solvent extraction, adsorption methods, extractive distillation and chemical transformation. These methods exploit differences in the crystallization, solubility, boiling point, volatility reactivity and affinity and adsorption properties of the isomers. However, the difference between these properties in E and Z isomers is often relatively small, making such separations difficult and expensive Processes such as fractional distillation and/or extractive distillation are energy intensive, and therefore can be expensive. Since the boiling points of E and Z isomers are often quite similar, distillation processes are often inefficient, or provide product streams in which the purity of the desired isomer is low. Furthermore certain isomers may have a very high boiling point or may decompose or unstable under distillation condition. Accordingly, adsorption processes such as chromatography have been receiving more attention recently because they have the potential to offer higher purity and higher efficiency (can also be operated under milder conditions) compared to other separation methods.

A variety of methods have been used to separate E and Z isomers. For example, U.S. Pat. No. 4,433,195 describes a process for separating non-polar cis- and trans-olefins (e.g., mixtures of Z and E butene; i.e. cis and trans 2-butene, respectively) using a silicalite adsorbent (silicalite is an organophilic form of silica). The separation may be carried out in either a single column, or using counter current moving bed or simulated moving bed flow systems.

Similarly, U.S. Pat. No. 3,600,453 also describes batch-type chromatographic separations of cis- and trans-olefins with a stationary phase of X or Y zeolites exchanged with various cations (i.e., copper, silver, gold, zinc, cadmium, and mercury). In this process, one of the isomers is selectively bound to the ion exchanged zeolite, and periodically desorbed from the stationary phase by interrupting the feed stream flowing into the column, and then stripping the selectively bound isomer from the column.

Various other workers have described methods of separating cis- and trans-unsaturated esters by conventional, batch-type chromatographic methods using a silver "loaded" stationary phase. For example, Morris, *Journal of Lipid Research*, vol. 7, (1966) pages 717-732, describes separating mixtures of cis- and trans-cyclodecenols and cis- and trans-unsaturated fatty acid esters on a column of silica gel impregnated with a stationary phase of aqueous silver nitrate. Houx et al., *Journal of Chromatography*, vol. 129, (1976) pages 456-459, describes separating unsaturated esters by HPLC using silver nitrate coated silica. Heath et al., *Journal of Chromatographic Science*, vol. 15 (1977), pages 10-13 describes the chromatographic separation of E and Z 9-tetradecenol acetate using silver nitrate coated silica. Lam et al., *Journal of Chromatographic Science*, vol. 15, (1977), pages 234-238 describe separating cis- and trans-p-bromophenacyl esters of unsaturated fatty acids on a silver loaded alumina silicate stationary phase or a silver ion exchanged ion exchange resin. Nikolova-Damyanova et al., *Journal of Chromatography*, 609, (1992), pages 133-140 describe the chromatographic separation of cis- and trans-unsaturated fatty esters using a silver nitrate coated silica stationary phase. Emken et al, *Journal of the American Oil Chemist's Society*, May 1964, vol. 41, no. 5, pages 388-390, describes the chromatographic separation of cis- and trans-fatty esters using a silver "saturated" ion exchange resin.

Thus, separations of E and Z isomers of unsaturated compounds having polar functional groups, e.g., alkene alcohols or esters, have only been carried out using conventional batch-type chromatographic methods. However, such chromatographic methods have insufficient productivity and purity for commercial use. Additionally, they consume more eluent and generate products with lower concentration. Since they are run in a "batch" mode, rather than a continuous or semi-continuous mode, such methods are also more expensive and complex to operate compared to a continuous process.

SUMMARY OF THE INVENTION

Mixtures of E and Z isomers of at least one alkene alcohol and/or at least one alkene alcohol derivative can efficiently be separated, in commercially useful yield, concentration, and purity, by a substantially continuous process in which a feed stream comprising a mixture of E and Z isomers of at least one alkene alcohol or a derivative thereof, and optionally other components, is contacted with an ion exchange medium which has been ion exchanged with silver and/or copper ions. Separate product streams enriched in, respectively, the E or Z isomer are thereby produced.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawing, wherein:

The FIGURE is a schematic diagram of a preferred embodiment of the process of the present invention.

DETAILED DESCRIPTION OF THE INVENTION

Thus, in a first embodiment of the process of the present invention, an ion exchange medium which is ion exchanged with silver and/or copper ions is substantially continuously contacted with a feed stream comprising a mixture of E and Z isomers of at least one alkene alcohol and/or E and Z isomers of at least one alkene alcohol derivative. One or more product stream(s) having a higher isomeric purity of one of the E or Z isomers of the alkene alcohol or derivative thereof, compared to the isomeric purity of the isomers in the feed stream are then removed.

By "substantially continuously" or "substantially continuous" we mean that an ion exchange medium which is ion exchanged with silver and/or copper ions is contacted with a feed stream comprising a mixture of E and Z isomers, without completely stopping the feed stream flow to the ion exchange medium for a significant period of time. In other words, in the substantially continuous process of the present invention the flow rate of the feed stream flow may remain constant or vary while the separation is carried out, or even stop momentarily (e.g., for the time required to redirect the feed flow using one or more valves). However, the substantially continuous process of the present invention differs from that of conventional batch-type chromatographic processes in that in batch-type chromatographic processes, the feed stream flows only intermittently, and is stopped periodically for significant periods of time so that the isomer retained on the stationary phase of the chromatography column can be eluted or stripped off. Examples of the substantially continuous processes of the present invention include, without being limited thereto, continuous solid/liquid contacting methods, simulated moving-bed counter current flow methods, counter current moving bed systems, etc. The substantially continuous process of the present invention thus provides significantly higher productivity compared to conventional batch-type chromatographic processes because the feed flow does not need to stop while the retained components of the separation are stripped from the stationary phase. In addition, unlike conventional chromatographic methods, the substantially continuous process of the present invention can be readily integrated with continuous downstream and upstream processes.

The substantially continuous process of the present invention may include for example, a continuous process carried out in a continuous multi-column contactor which comprises a plurality of columns which are mounted and rotate about a central axis. The columns contain an ion exchange material, such as, for example, an ion exchange resin. Liquid (e.g., a feed flow comprising the mixture of E and Z isomers of an alkene alcohol or alkene alcohol derivative) is supplied individually to the top of the columns through conduits connected with a valves assembly. Similarly, conduits connect the lower end of each column with a similar valves assembly. Alternatively, all of the conduits may be connected to a single valve assembly that controls all of the liquid flows into and out of the columns. The valve assemblies include movable plates with slots that cover and uncover inlet ports as the plate rotates with the carousel. By varying the size of the slots in the plate and the location of the slots, the flow from the supply conduits into the column and flow from the column to the exhaust conduits can be controlled in a predetermined manner. The time during which liquid flows into and out of the containers may be a function of the speed of rotation of the columns about the central axis, or a function of the speed of actuation of the valves, if the valves are actuated independently of the rotation of the columns. A countercurrent flow of a solid sorbent phase (e.g., an ion exchange medium) and a liquid phase is provided by the rotation of the columns and the actuation of the valves. The columns may rotate through various zones, such as an adsorption zone, a wash zone, a regeneration zone, etc. to effect a continuous separation. Generally, such processes are described for example, in U.S. Pat. Nos. 6,431,202, 5,676,826 and 4,808,317, herein incorporated by reference in their entirety, although not in relation to the separation being performed by the present invention.

The adsorbent medium of the process of the present invention is an ion exchange medium which has been ion exchanged with silver and/or copper ions. The ion exchange medium can be either an organic or inorganic ion exchange medium.

Examples of organic ion exchange media may include an organic ion exchange resin, crosslinked or uncrosslinked having carboxylic, sulfonic, or phosphonic acid groups. For example, the organic ion exchange medium may include conventional ion exchange resins such as macroporous or gel type styrene-divinyl benzene copolymers substituted with sulfonic acid groups, sold under the trade names LEWATIT (Bayer), DOWEX (Dow Chemical), IONEX and AMBERLITE (Rohm and Haas), DIAION and RELITE ((Mitsubishi Chemical), and various exchange resins sold by Purolite. However, resin which is insoluble in the feed stream, and which is capable of being ion exchanged with silver or copper ions can be used. Preferred organic ion exchange resins may include acidic macroporous styrene-divinylbenzene copolymers such as LEWATIT SP 112 (Bayer), DOWEX MSC-1 (Dow Chemical), TONEX FTB4 (Rohm and Haas), PCR-145K (Purolite). More preferably, the ion exchange resins used in the present invention have particle sizes in the range from 100 µm to 700 µm.

Inorganic ion exchange media may include any inorganic material capable of ion exchanging silver or copper ions. For example, such materials may include silica, mesoporous material, alumina, alumino-silicates, zeolites, clays, etc. Preferred inorganic media include large pore opening zeolites such as X zelolite, Y zeolite and silicalites.

The amount of silver and/or copper ions with which the ion exchange media are exchanged may fall within the range of from 1-100% (based on total amount of ions present in ion exchange resin), preferably from 5-95%, more preferably from 5-85%, still more preferably from 5-35%, even more preferably from 5-30%, even still more preferably from 10-25% most preferably from 10-20%. The preferred ion is silver.

The adsorbent of the process of the present invention may be ion exchanged by contacting the ion exchange medium with a solution of silver and/or copper ions dissolved in a suitable solvent, for a suitable period of time. Suitable solvents are solvents which solvate the silver and/or copper ions, and are capable of wetting the ion exchange medium. For example, suitable solvents may include water or alcohols, or mixtures thereof. The preferred solvent is water.

The ion exchange process may be carried out as a batch process, e.g., by simply soaking the ion exchange medium in a solution of the silver and/or copper ion for a suitable period of time, then decanting the excess ion solution, followed, if necessary, by washing the ion exchange medium to remove any excess ions which are not ionically bound to the ion exchange medium. Alternatively, the ion exchange may be carried out in situ; that is, in the apparatus in which the separation is to be carried out. For example, the ion exchange medium may be loaded into the columns of a simulated moving bed countercurrent flow system, then a solution of the silver and/or copper ions is allowed to flow through the columns until an appropriate level of ion exchange has occurred. The columns may then be flushed with a suitable solvent to remove ions which are not ionically bound to the ion exchange medium. A suitable process for preparing the medium is described in U.S. patent application Ser. No. 10/411,900, filed Apr. 11, 2003, the contents of which are hereby incorporated by reference.

The feed stream of the process of the present invention comprises a mixture of E and Z isomers of at least one alkene alcohol and/or a mixture of E and Z isomers of at least one alkene alcohol derivative. By alkene alcohol, we mean an organic compound having at least one carbon-carbon double bond group, and at least one hydroxyl group. For example, an alkene alcohol may include 2-butenols, 2-pentenols, methyl-2-butenol, 2-hexenols, 3-hexenols, methyl-2-pentenol, 2-heptenols, 3-heptenols, etc. Alkene alcohol derivatives include compounds such as ethers, esters, acetals, aldehydes, ketones, and carboxylic acids which can be prepared from alkene alcohols. For example, ether derivatives of alkene alcohols may include ethers capable of being prepared by reacting an alkene alcohol with another alkene alcohol, or capable of being prepared by reacting an alkene alcohol with an alcohol which is not an alkene alcohol. Ester derivatives of alkene alcohols may include esters which are capable of being prepared by reacting an alkene alcohol with a carboxylic acid (or other type of acid, such as sulfonic or phosphonic acids), or are capable of being prepared by reacting an alcohol with an alkene alcohol that has been oxidized to the corresponding carboxylic acid. Acetal derivatives of alkene alcohols may include acetals which are capable of being prepared by reacting a ketone with at least one alkene alcohol. Aldehyde, ketone, and carboxylic acid derivatives of alkene alcohols include, respectively, aldehydes, ketones, and carboxylic acids which are capable of being prepared by the oxidation of an alkene alcohol.

The feed stream may optionally include at least one solvent in which the mixture is dissolved. Suitable solvents include those in which the mixture of isomers is soluble. For example, the solvent may include polar protic solvents such as water, methanol, ethanol, propanol and butanol as well as glycol, aliphatic or aromatic hydrocarbons such as petroleum ethers, pentane, hexane, hexanes, toluene, benzene, xylenes, etc., ether solvents such as diethyl ether, tetrahydrofuran and DME, ester solvents such as methyl acetate, ethyl acetate, propyl acetate, butyl acetate, polar aprotic organic solvents such as NMP, DMSO, DMF and organic solvents such as acetone or methyl ethyl ketone.

In addition to the mixture of E and Z isomers, the feed stream may also include other constitutional isomers of the alkene alcohol, such as isomers in which the carbon-carbon double bond is located at other positions within the molecule. For example, the feed stream may comprise mixtures of E and Z isomers of the various heptenol isomers, or a mixture of the E and Z isomers of hexenol, such as 3-hexene-1-ol, 2-hexene-1-ol, 4-hexene-1-ol. In addition, the feed stream may contain other soluble contaminants or impurities, such as saturated alcohols or other related compounds. One advantage of the present process is the ability to also remove these contaminants and/or impurities from the E and Z isomers of the alkenol or alkenol derivative.

Having generally described this invention, a further understanding can be obtained by reference to certain specific examples which are provided herein for purposes of illustration only, and are not intended to be limiting unless otherwise specified.

EXAMPLE

A ⅛" continuous chromatographic separator unit (commercially available CSEP unit from Calgon Carbon Corporation) was used containing a set of 10 columns that were affixed to a rotating platform and a central rotary valve. The rotary valve provided ten fixed ports that accepted the inlet and outlet process streams. The relative location of inlet and outlet streams and the interconnectivity of the columns are shown in the FIGURE. The columns rotated step-wise through each port position on a specified time interval called the switching time.

The columns were 1.1 cm in diameter and 100 cm in length. Each column contained 95 ml of silver loaded PCR-145K resin. The resin was about 300 μm in diameter and was prepared (silver ion exchanged) in-situ in the same CSEP unit to contain 13.6 wt % silver ion on a dry resin basis. The entire unit was contained in an enclosure maintained at a constant temperature 40° C.

A mixture of E/Z-heptenols (Feed stream S1) was continuously fed to port 6 at a rate of 0.215 ml/min. A recycle stream (S5) was withdrawn from port 10 at a rate of 4.53 ml/min. This recycle stream was then combined with a methanol stream (S4) to form the elution stream which was fed to port 1 at a rate of 11.02 ml/min. The E-product stream (S7) was withdrawn from port 8 at a rate of 1.09 ml/min and the Z-product stream (S3) was withdrawn from port 2 at a rate of 3.85 ml/min. A purge stream (S2) which may be used to purge out other impurities from the feed stream was withdrawn from port 9 at a rate of 1.59 ml/min. The columns were rotated with a switching time of 12 minutes. The results of the recovery of E/Z heptenols in each stream and its purity are reported in Table 1.

The purity was calculated as:

$E$ heptenol purity (%)=(($E$ heptenol concentration)/($E$ heptenol concentration+$Z$ heptenol concentration))*100%

$Z$ heptenol purity (%)=(($z$ heptenol concentration)/($E$ heptenol concentration+$Z$ heptenol concentration))*100%

The recovery was calculated as $E$-heptenol recovery=(($E$-heptenol in a stream)/(($E$-heptenol in $E$-product stream)+($E$-heptenol in $Z$-product stream)+($E$-heptenol in purge product stream)))*100%

$E$-heptenol in a stream=$E$-heptenol concentration*flow rate $Z$-heptenol recovery=(($Z$-heptenol in a stream)/(($Z$-heptenol in $E$-product stream)+($Z$-heptenol in $Z$-product stream)+($Z$-heptenol in purge product stream)))*100%

$Z$-heptenol in a stream=$Z$-heptenol concentration*flow rate

TABLE 1

E and Z heptenol purity and recovery in each stream

| Streams | E-heptenol purity (%) | Z-heptenol purity (%) | E-heptenol recovery (%) | Z-heptenol recovery (%) |
|---|---|---|---|---|
| Feed stream | 76.0 | 24.0 | | |
| E-product stream | 87.3 | 12.7 | 97.0 | 45.0 |
| Z-product stream | 0.6 | 99.4 | | 55.0 |
| purge stream | 99.7 | 0.3 | 3.0 | |

The results in Table 1 show clearly the separation of the E/Z heptenols in the feed stream into two product streams (E- and Z-product streams) by this continuous process. Compared to the feed stream, the E-product stream had a higher E-heptenol purity and the Z-product stream had a higher Z-heptenol purity. The results also demonstrated the recovery of very high purity Z-heptenol isomer with good recovery yield.

What is claimed as new and is intended to be secured by Letters Patent is:

1. A separation process comprising:
substantially continuously contacting an ion exchange medium which is ion exchanged with silver and/or copper ions with a feed stream comprising E and Z isomers of at least one alkene alcohol derivative, and, optionally, one or more contaminants or impurities;
removing at least one product stream having a higher isomeric purity of the E or Z isomer of at least one alkene alcohol derivative, relative to the isomeric purity of the E or Z isomer of the alkene alcohol derivative in the feed stream.

2. The separation process of claim 1, wherein the ion exchange medium is ion exchanged with silver.

3. The separation process of claim 1, wherein the ion exchange medium is an ion exchange resin ion exchanged with silver.

4. The separation process of claim 1, wherein said substantially continuously contacting is carried out in a continuous solid/liquid contactor or in a simulated moving-bed counter current flow system.

5. The separation process of claim 3, wherein the ion exchange resin is a macroporous styrene-divinylbenzene copolymer having sulfonic acid or sulfonic acid salt groups.

6. The separation process of claim 5, wherein the ion exchange resin has a particle size of 100 to 700 μm.

7. The separation process of claim 1, wherein the feed stream comprises at least one alkene alcohol derivative wherein the alkene alcohol portion is selected from the group consisting of E and/or Z isomers of 2-butenols, 2-pentenols, 2-hexenols, 3-hexenols, 2-heptenols, 3-heptenols, and mixtures thereof.

8. The separation process of claim 7, wherein said at least one alkene alcohol derivative is at least one member selected from ethers, esters, acetals, aldehydes, ketones, and carboxylic acids of at least one alkene alcohol.

9. The separation process of claim 7, wherein said alkene alcohol portion is selected from the group consisting of E and/or Z isomers of 3-hexene-1-ol, 2-hexene-1-ol, 4-hexene-1-ol, and mixtures thereof.

10. The separation process of claim 1, wherein the product stream comprises at least 98.5 wt. % of a Z-3-hexen-1-ol derivative.

11. The separation process of claim 10, wherein the product stream comprises at most 1.0 wt. % of an E-3-hexen-1-ol derivative.

12. The separation process of claim 1, wherein the feed stream further comprises at least one solvent selected from the group consisting of alcohols, aliphatic hydrocarbons, aromatic hydrocarbons, ether solvents, ester solvents, and polar aprotic organic solvents.

13. The separation process of claim 12, wherein said at least one solvent is at least one solvent selected from the group consisting of methanol, ethanol, propanol, butanol, glycols, petroleum ethers, pentane, hexane, hexanes, toluene, benzene, xylenes, diethyl ether, tetrahydrofuran, DME, methyl acetate, ethyl acetate, propyl acetate, butyl acetate, NMP, DMSO, DMF, acetone, MEK, water and mixtures thereof.

14. The separation process of claim 13, wherein said at least one solvent is methanol.

15. The separation process of claim 1, wherein said one or more contaminants or impurities are present in said feed stream and said E or Z isomer is also separated from said one or more contaminants or impurities.

16. The separation process of claim 15, wherein said one or more contaminants or impurities are saturated alcohols.

17. The separation process of claim 16, wherein said saturated alcohols have a number of carbons identical to said E or Z isomer.

18. The separation process of claim 1, wherein said feed stream further comprises E and Z isomers of at least one alkene alcohol.

19. The separation process of claim 18, wherein said at least one alkene alcohol is the same as the alkene alcohol portion of said at least one alkene alcohol derivative.

* * * * *